(12) United States Patent
Huang

(10) Patent No.: US 7,306,563 B2
(45) Date of Patent: Dec. 11, 2007

(54) PULSE DIAGNOSTIC SYSTEM

(76) Inventor: Herb H. Huang, 17961 Inverness Curve, Eden Prairie, MN (US) 55347

( * ) Notice: Subject to any disclaimer, the term of this patent is extended or adjusted under 35 U.S.C. 154(b) by 918 days.

(21) Appl. No.: 10/375,686

(22) Filed: Feb. 27, 2003

(65) Prior Publication Data

US 2003/0212335 A1    Nov. 13, 2003

Related U.S. Application Data

(60) Provisional application No. 60/360,685, filed on Mar. 2, 2002.

(51) Int. Cl.
 *A61B 5/02* (2006.01)
(52) U.S. Cl. .................. 600/500; 600/485; 600/490
(58) Field of Classification Search ................ 600/485, 600/490, 500
 See application file for complete search history.

(56) References Cited

U.S. PATENT DOCUMENTS

| | | | |
|---|---|---|---|
| 4,660,566 A * | 4/1987 | Palti ............................ | 600/490 |
| 4,799,491 A * | 1/1989 | Eckerle ....................... | 600/485 |
| 5,131,400 A * | 7/1992 | Harada et al. .............. | 600/500 |
| 5,179,956 A * | 1/1993 | Harada et al. .............. | 600/485 |
| 5,269,312 A | 12/1993 | Kawamura et al. | |
| 5,503,156 A | 4/1996 | Millar | |
| 5,617,868 A | 4/1997 | Harada et al. | |
| 5,640,964 A | 6/1997 | Archibald et al. | |
| 5,724,980 A | 3/1998 | Nakamura et al. | |
| 5,984,874 A | 11/1999 | Cerwin ........................ | 600/549 |
| 6,132,383 A | 10/2000 | Chesney et al. | |
| 6,159,166 A | 12/2000 | Chesney et al. | |
| 6,162,185 A * | 12/2000 | Amano et al. .............. | 600/557 |
| 6,176,832 B1 * | 1/2001 | Habu et al. .................. | 600/485 |
| 6,210,340 B1 * | 4/2001 | Amano et al. .............. | 600/500 |
| 6,301,494 B1 | 10/2001 | Schafer | |
| 6,409,684 B1 * | 6/2002 | Wilk ........................... | 600/586 |
| 6,561,985 B2 * | 5/2003 | Ito ............................... | 600/494 |
| 6,616,612 B1 * | 9/2003 | Nissila et al. ............... | 600/485 |
| 6,802,816 B2 * | 10/2004 | Palti et al. ................... | 600/493 |
| 2002/0026121 A1 * | 2/2002 | Kan ............................ | 600/500 |

FOREIGN PATENT DOCUMENTS

| | | |
|---|---|---|
| CN | 86107766 A | 5/1988 |
| CN | 1310981 A | 9/2001 |
| CN | 1337208 A | 2/2002 |
| CN | 1339287 A | 3/2002 |

OTHER PUBLICATIONS

PCT International Search Report for International Application No. PCT/US03/06133 mailed on Jul. 8, 2003 (7 pages).

* cited by examiner

*Primary Examiner*—Charles A. Marmor, II
*Assistant Examiner*—Karen E Toth
(74) *Attorney, Agent, or Firm*—Dicke, Billig & Czaja, P.L.L.C.

(57) ABSTRACT

A pulse diagnostic instrument of the present invention comprises a plurality of probes connected together and aligned laterally in series, with each probe configured for contacting a skin surface of a body limb adjacent an arterial vessel. Each probe includes a pressure sensor configured for sensing a pulse pressure of the arterial vessel and an electrically-driven pressure applicator, mounted to the pressure sensor, and configured for applying an external force through the pressure sensor to apply pressure against the arterial vessel through the skin surface during sensing of the pulse pressure.

9 Claims, 13 Drawing Sheets

PULSE DIAGNOSTIC SYSTEM

CROSS-REFERENCE TO RELATED APPLICATIONS

This Non-Provisional Application claims the benefit of the filing date of Provisional U.S. Patent Application Ser. No. 60/360,685, entitled "DIGITAL PULSE PRESSURE GRAPHIC AND VIDEO DIAGNOSTIC SYSTEM FOR USE WITH PRESSURE SENSOR ARRAYS," having a filing date of Mar. 2, 2002, and which is herein incorporated by reference.

BACKGROUND OF THE INVENTION

Medical practitioners have long used pulse measurements, such as heart rate and blood pressure, to ascertain the health of a patient. This practice obviously stems from the crucial role that a heart and circulatory system plays on the entire physiology of the patient.

Differing from conventional pulse detection and measurement for humans, traditional Chinese medical practitioners have for thousands of years practiced the so-called Chinese Pulse-Taking and Medical Diagnosis (herein CPT/MD). This diagnostic method is performed by pressing the index, middle and third fingers (10,12,14) of one a practitioner's hands 15 in a row onto a Cunkou acupoint 16 of their patient's wrist 18, as illustrated in FIGS. 1A and 1B. These fingers are used to qualitatively sense and capture the two-dimensional distribution of pulse pressure, or pulse pressure topography, as well as its dynamic characteristics within arterial vessel 34 under skin 30 and tissue 32. The acupoint, Cunkou, refers to the medial area of the prominent head of the radius at the wrist over the radial artery. By individually adjusting the pressure applied by each finger to the acupoint, they can also actively force the downstream or upstream shift of the pulse thus felt along the vessel to sense and capture more comprehensive dynamic characteristics of the arterial pulse. Such a pulse pressure topography and dynamic characteristics are critically informative to the practitioners in identifying the so-called medical pulse conditions and thus, diagnosing the illness and health condition of the patient. In this context, the pulse conditions refer to the physical conditions of pulsation felt by the fingertips, including frequency, rhythm, extent of filling, evenness, motility and amplitude.

For thousands of years, however, the CPT/MD has been conducted only through the fingers of practitioners. Accordingly, this method is highly subjective and considered as a work of art, rather than a science, due to the obvious subjective nature of each practitioner's individual experience and consistency. Moreover, the practitioners can only verbally describe what they feel through their fingertips, even though the assessment is so critical to their medical diagnosis and judgment. Their verbal expressions of what is felt through the fingertips uses commonly agreed upon, but very limited, terminology for the type of pulse and strength of pulse manifested as the pulse condition. This verbal information is highly qualitative and is by no means objective. Consequently, this verbal data regarding a pulse condition cannot be credibly kept as objective medical data for patients.

While conventional pulse detection and measurement devices facilitate more scientific rigor in assessing a pulse, these devices fall short in achieving significant aspects of pulse diagnostics.

SUMMARY OF THE INVENTION

A pulse diagnostic instrument of the present invention comprises a plurality of probes connected together and aligned laterally in series, with each probe configured for contacting a skin surface of a body limb adjacent an arterial vessel. Each probe includes a pressure sensor configured for sensing a pulse pressure of the arterial vessel and an electrically-driven pressure applicator, mounted to the pressure sensor, and configured for applying an external force through the pressure sensor to apply pressure against the arterial vessel through the skin surface during sensing of the pulse pressure.

BRIEF DESCRIPTION OF THE DRAWINGS

Embodiments of the invention are better understood with reference to the following drawings. The elements of the drawings are not necessarily to scale relative to each other. Like reference numerals designate corresponding similar parts.

DETAILED DESCRIPTION

A system and method of the present invention detects, maps, transmits, displays, analyzes and/or characterizes a two-dimensional pulse pressure topography, and its dynamic evolution over time, of a human pulse within an arterial vessel. Moreover, this system and method allows interactive, controllable and precise pressurization against the arterial vessel independently in each individual region of vessel pulse detection.

The two-dimensional pulse pressure distribution (pulse pressure topography) produced using a system and method of the present invention includes both a longitudinal component along the arterial vessel and a lateral component transversely across the vessel. This data is used to quantitatively analyze the evolution and dynamics of the pulse pressure topography over one or more arterial pulse cycles The system of the present invention includes at least one or more pulse sensing probes. Each of the pulse sensing probes comprises an electrically-drive pressure applicator (e.g., a translation actuator), at least one integrated pressure sensor array and an on-board signal pre-amplifier/processor. The translation actuator acts as a pressure applicator to exert a mechanical pressure against the arterial vessel (in which the pressure is being measured) for determining how the pulse pressure and characteristics respond to the external pressure. The probes are carried by, and removably secured about the wrist with, a removable cuff or with a wrist fixture for adjustably locating a set of pulse map-sensing probes or "electronic fingers" along the vessel around a pulse reference point, such as the Cunkou acupoint, Each pressure applicator (e.g., translation actuator) is individually controllable to differentially apply pressure by each probe against the arterial vessel during sensing of the pulse pressure topography. Positive and negative pressurization can be electronically activated independently and controllably upon any one of those integrated pressure sensor arrays via adaptive electrical pressure applicators or translation actuators: 1) to adjust the overall amplitudes of pulse pressure acting upon the integrated pressure sensor arrays and thus the pulse pressure signal detected by the integrated pressure sensor arrays; and 2) to actively activate the shift of the pulse pressure along the vessel for digitally and graphically tracking, mapping and analyzing the dynamic characteristics of the pulse pressure topography and the longitudinal shift of the pulse pressure peak along the arterial vessel.

Figure 1A:
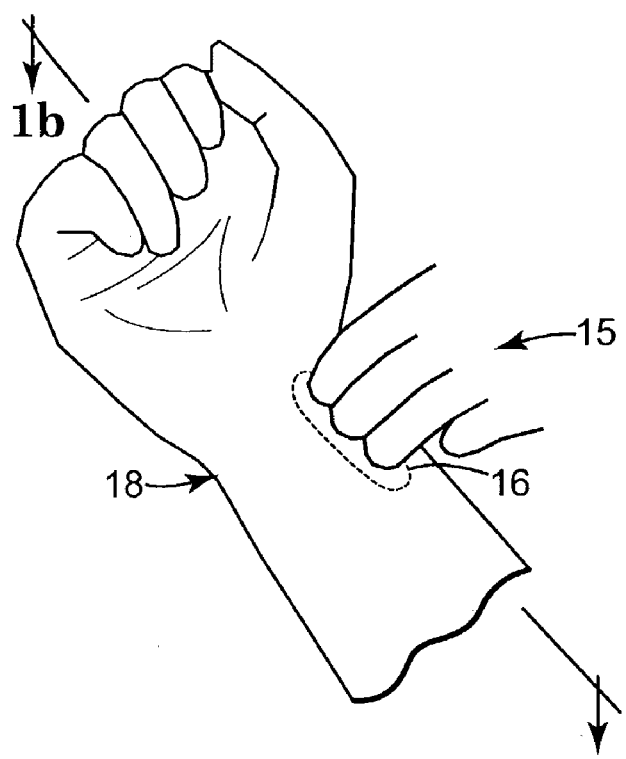
FIG. 1*a* is a schematic illustration of a prior art pulse diagnostic method.
Figure 1B:
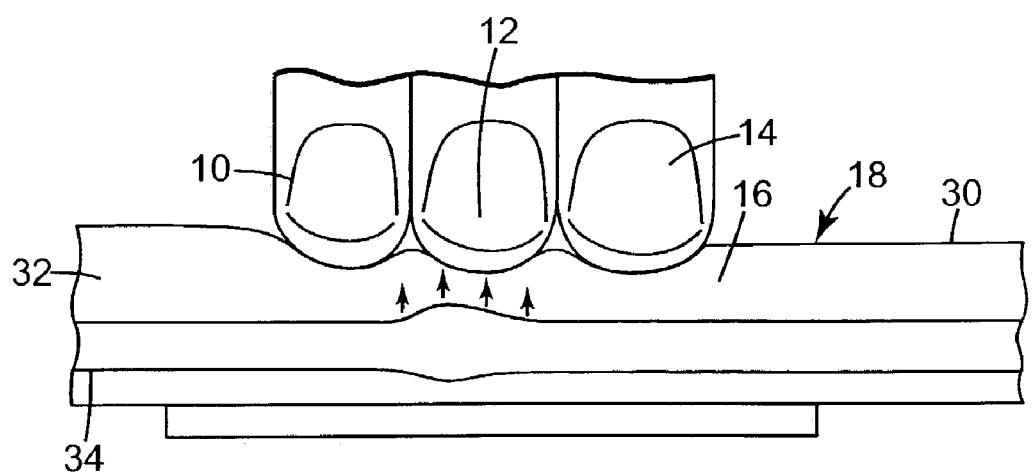
FIG. 1*b* is a sectional view of FIG. 1 as taken along lines 1*b*-1*b*.
Figure 2:
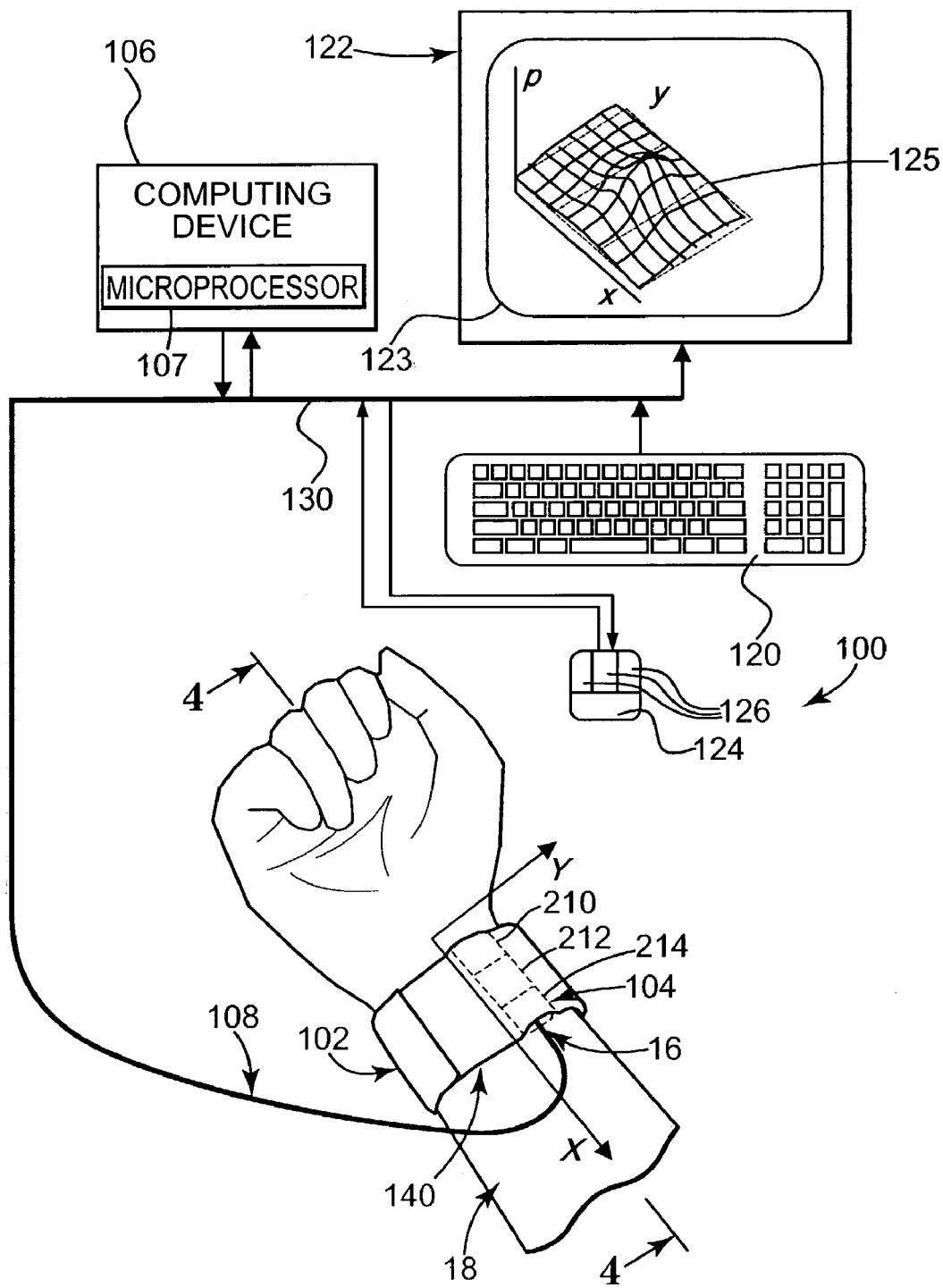
FIG. 2 is a schematic illustration of a pulse diagnostic system, according to an embodiment of the present invention.

FIG. 2 illustrates an exemplary embodiment of the present invention including a pulse system 100. As shown in FIG. 2, system 100 includes pulse diagnostic instrument 102, computing device 106 with microprocessor 107, input device 120 (e.g., keyboard), mouse 124, video monitor 122, and communication interface 130. Diagnostic instrument 102 includes set 104 of probes 210,212,214 carried by flexible cuff 140. Cable 108 electrically and mechanically connects diagnostic assembly 102 to communication interface 130.

As illustrated in FIG. 2, diagnostic instrument 102 is removably secured about a body limb (e.g., arm, leg), such as a patient's wrist 18 for non-invasively sensing a pulse pressure of an arterial vessel within that body limb. In particular, flexible cuff 140 encircles wrist 18 to cause set 104 of probes 210,212,214 to be placed in pressing contact against skin 30 over arterial vessel 34 at pulse reference point 16. Each probe 210, 212, 214 senses a pulse of arterial vessel 34 and is configured for individually exerting an external pressure on arterial vessel 34 independent from the other probes, thereby resulting in a differential external pressure applied along arterial vessel 34 during sensing of a pulse pressure profile with probes 210, 212, 214. The construction and function of probes 210, 212, 214 that permit sensing the pulse and simultaneously selectively applying this differential pressure profile is described in more detail in association with FIG. 3. While diagnostic instrument 102 is shown having three probes, it optionally can include a fewer or greater number of probes including, but not limited to two, four, or more probes.

Diagnostic instrument 102, as supported by computing device 106 senses and maps a pulse pressure profile 125, which is displayed in real time or slow or fast motion on video monitor 122 as pulse pressure topography video 123. Input device 120 (e.g., keyboard) also provides a physical interactive interface for the system's operator to operate microprocessor 107 in conducting the desired data acquisition and analysis on the pulse pressure topography and its dynamic characteristics.

Communication link 108 (e.g., electrical cable) electrically and mechanically couples diagnostic instrument 102 to computing device 106, including microprocessor 107, while communication interface 130 establishes electrical communication between computing device 106, input device 120, mouse 124 and video display monitor 122.

Figure 3:
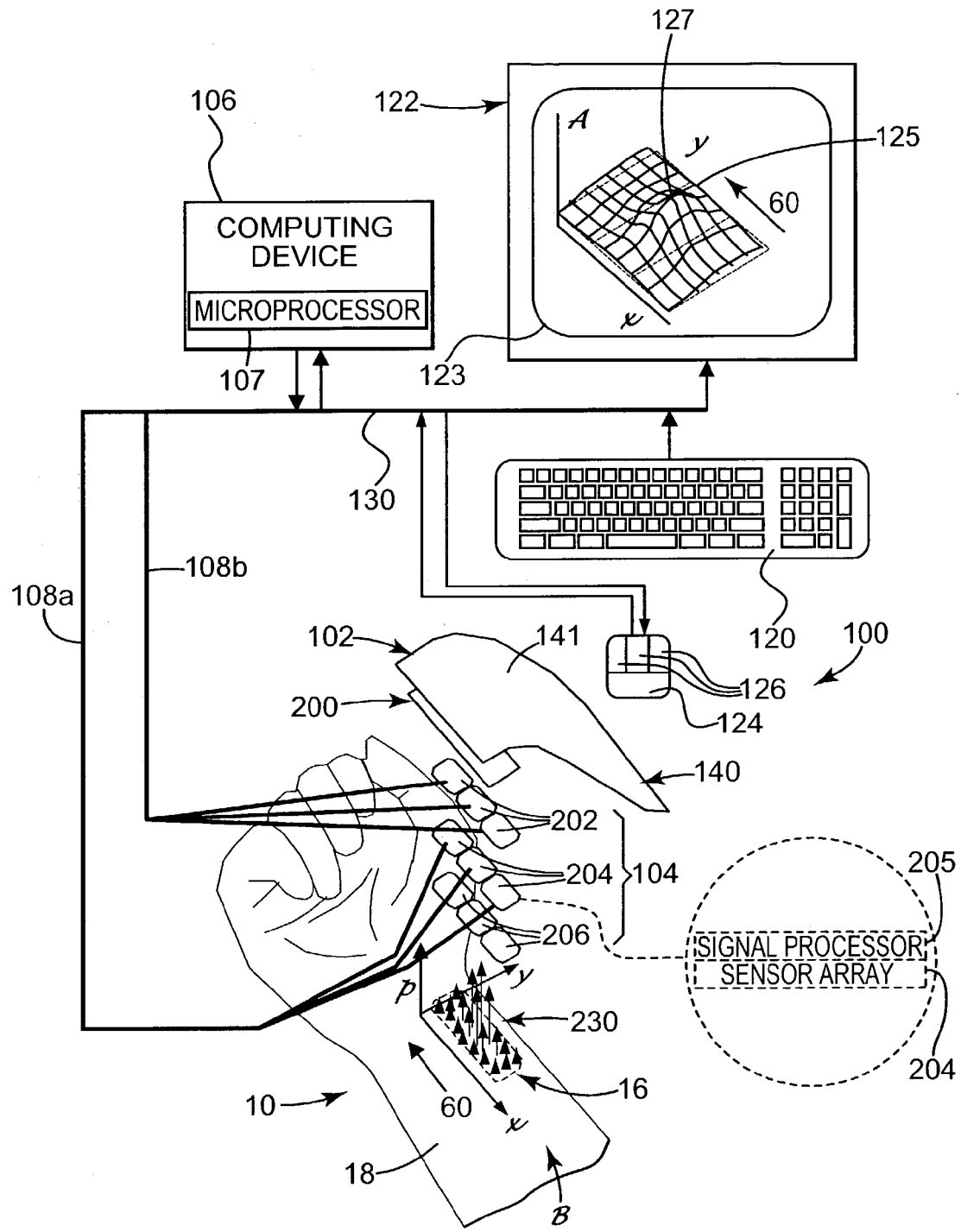
FIG. 3 is a schematic illustration of a pulse diagnostic system, including exploded views, according to an embodiment of the present invention.

FIG. 3 illustrates system 100 of FIG. 2 in more detail. In particular, probe set 104 of diagnostic instrument 102, as shown in an exploded perspective, comprises rigid backing 200 with each probe 210, 212, 214 including one external pressure applicator 202, one pressure sensor array 204 and one translation tip 206. In the same way that probes 210, 212, 214 are aligned linearly in series (FIG. 2), so to are each of components of probes 210, 212, 214 so that the three external pressure applicators 202, three pressure sensor arrays 204, and translation tips 206 form layers relative to one another to yield probe set 104.

As shown in FIG. 3, a pulse pressure 230 of arterial vessel 34 (shown in FIG. 2), which evolves temporally over pulse cycles (sensed by diagnostic instrument 102 through skin 30) and is expressed as a two-dimensional topography in both the longitudinal x (i.e., generally parallel to a longitudinal axis of arterial vessel 34) and lateral y directions (i.e., generally transverse to a longitudinal axis of arterial vessel 34) relative to arterial vessel 34. In particular, a spatial topography (and its temporal evolution) of the pulse pressure 230 is first translated from arterial vessel 34 through the translation tips 206 for sensing and mapping by pressure sensor arrays 204. These pressure sensor arrays 204 generate a set of electrical analog signals representing the two-dimensional spatial topography (and its temporal evolution) of the pulse pressure 230. Each sensor array 204 optionally includes an on-board signal pre-amplifier/processor 205, which is mounted on the upper side (i.e., backside) of sensor array 204 and electrically connected to the integrated pressure sensor arrays 204. The on-board processor 205 receives the electrical analog signals generated by sensor array 204, and converts the signals to a set of digital signals representing the sensed pulse pressure.

This set of digital signals of pulse pressure, representing the two-dimensional topography and its temporal evolution of the pulse pressure 230, are then transported to computing device 106 through cable 108*a* and communication interface 130. Computing device 106 processes the transported set of digital signals of pulse pressure and reformats the signals to a set of digital graphic image and video data of two-dimensional pulse pressure topography in a temporally regulated sequence at a much higher frequency than the pulse rate. The set of digital graphic image data is further digitally analyzed to derive certain numeric and text data on the dynamic characteristics of two-dimensional topography and its temporal evolution of the pulse pressure 230. Through computing device 106, the derived numeric and text data and the set of digital graphic image data are then combined and transformed to continuous digital video signal 123 of pulse pressure topography 125 (i.e., pulse pressure profile or pattern) that is transmitted via communication interface 130 and displayed on the monitor 122.

As the pressure peak of the pulse pressure 230 in the two-dimensional topography shifts along the arterial pulse flow direction 60, hump 127 of the pulse pressure topography image and waveform 125 displayed on the monitor 122 shifts accordingly in direction 60 (if a synchronized mode of display is employed).

Pressurization or de-pressurization on the pulse map-sensing probes 204 is optionally electrically activated by first introducing a set of digital input data of human pressurization instruction via the keyboard 120 or via the pressurization controller mouse pad 124 (i.e., adapted to control activation of pressure applicators 202) by pushing buttons 126. Then, the computing device 106 converts the set of digital input data to a stream of adaptive analog inputs, which is transmitted as a stream of adaptive analog input to the individual pressure applicators 202, again via the electronic interconnect cable 108*b*. The magnitudes of adaptive analog inputs of electrical charge or current can be adequately adjusted individually for each of pressure applicators 202 for each of probes 210, 212, 214 (according to the measured data on the pulse pressure 230 displayed on the graphic and video display monitor 122) to achieve an optimal pulse pressure mapping result for medical diagnosis.

Mouse pad 124 optionally provides a means for controlling pressurization of pressure applicators 202, since mouse pad 124 has the identical number of electronic analog push buttons 126 that correspond to the number of pulse map-sensing probes 210, 212, and 214. By pushing or releasing the pressure the practitioner applies to those electronic analog push-buttons 126 of mouse pad 124 to different levels, a correspondent set of pressurization/depressurization is applied via pressure applicators 202 to the corresponding pulse map-sensing probes 210, 212, and 214.

Figure 4:
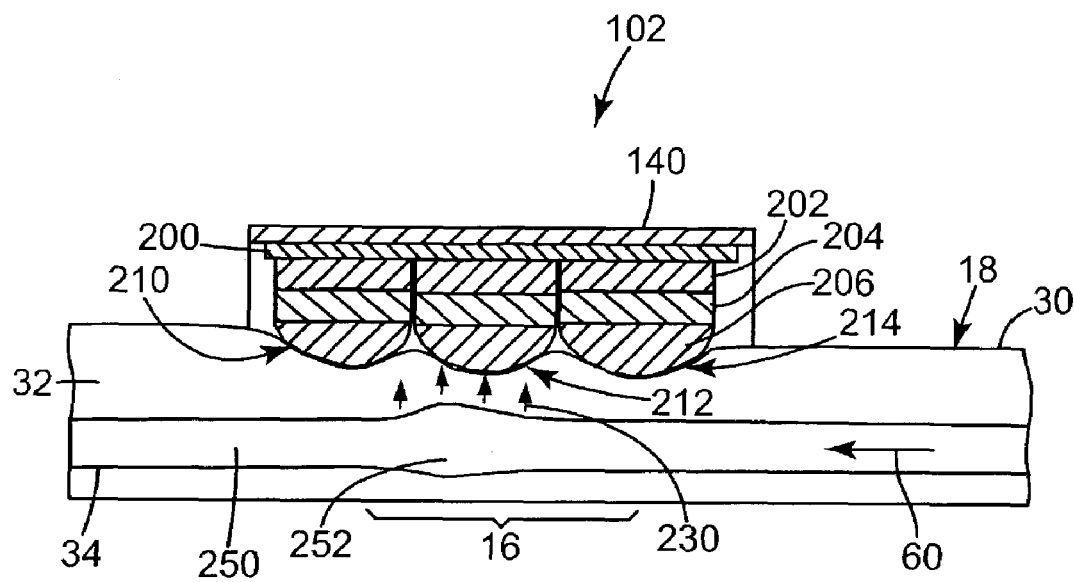
FIG. 4 is a sectional view of a pulse probe array of a pulse diagnostic system, according to an embodiment of the present invention.

FIG. 4 is sectional view of diagnostic instrument 102 of the present invention applied to a patient's wrist 18 by removable cuff 140. FIG. 4 illustrates three pulse-sensing probes of diagnostic instrument 102, namely first probe 210, second probe 212, and third probe 214 (e.g., approximating an index, middle and third finger of a practitioner's hand). As shown in FIG. 4, probes 210, 212, 214 are firmly pressed onto skin 30 (and tissue 32) across the wrist arterial pulsing region 16 of the patient. Stiff fixture panel 200, carried by flexible cuff 140, removably secures probes 210, 212, 214 against the patient's wrist 10 (FIG. 3).

As one arterial pulse 252 passes through arterial vessel 34 along the arterial pulse flow direction 60, pulse pressure 230 is transmitted to and thus sensed by those three pulse map-sensing probes 210, 212, 214. This sensing includes sensing the effect of additional tissue pressurization by external pressure applicators 202 of probes 210, 212, 214. While pulse reference point 16 preferably comprises the Cunkou acupoint, other locations for sensing an arterial vessel along a body limb can be selected for applying diagnostic instrument 102.

Figure 5:
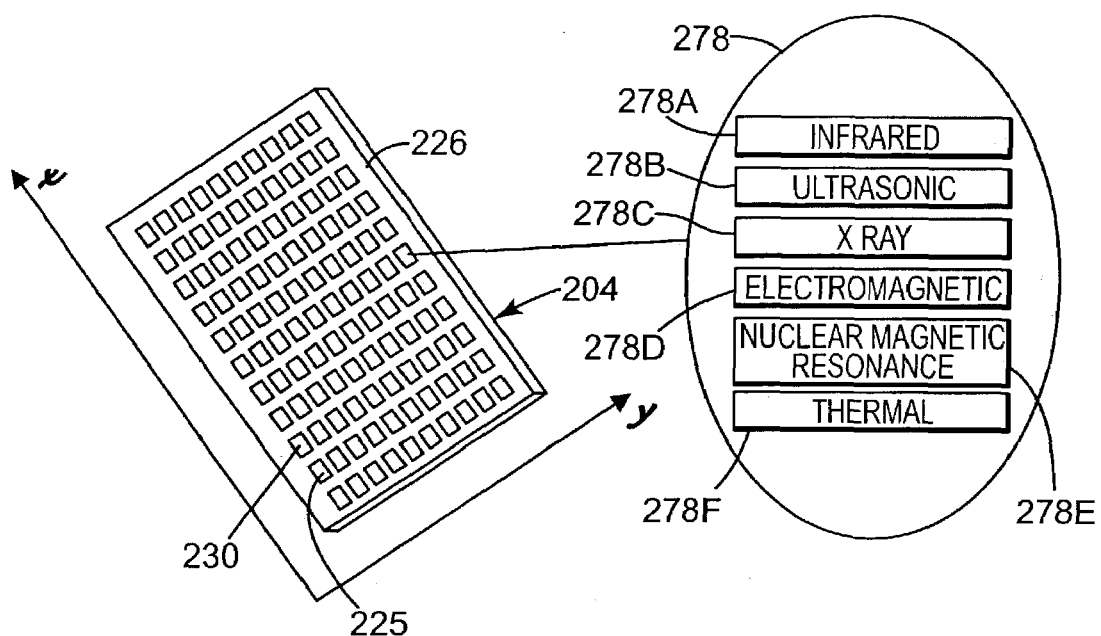
FIG. 5 is a plan view of an integrated sensor array of the pulse diagnostic system, according to an embodiment of the present invention.

FIG. 5 illustrates an integrated sensor array 204 of the present invention. As shown in FIG. 5, sensor array 204 comprises a plurality of miniaturized pressure sensor cells 225, which are fabricated together in a regularly spaced planar arrangement on a rigid or flexible substrate 226 as shown. These sensor cells 225, when formed as part of one of the probes 210, 212, 214 face down towards skin 30 at pulse reference point 16 (FIGS. 2-3) and are used to continuously measure the pulse pressure of arterial vessel 34. As shown in FIG. 3, the longitudinal and lateral directions, x and y, of the integrated pressure sensor array 204 are aligned along and cross the arterial vessel. Each miniaturized pressure sensor cell 225 detects a corresponding portion of translated pulse pressure 230 translated through tip 206, and measures the total force applied onto itself in summation of the transmitted pulse pressure 230. Thus, integrated pressure sensor array 204 (together with the other integrated pressure sensor arrays 204 for each probe 212, 214) maps the pulse pressure topography 230 of two-dimensional nature in both the longitudinal and lateral directions to arterial vessel 34 by discretely sensing the pulse pressure 230 at a matrix of locations in such a regularly spaced planar arrangement.

While sensor array 204 preferably includes at least about eighty sensor cells 225, a fewer or greater number of sensor cells 225 can be used as long as sufficient number of data points of the pulse is taken to achieve robust data sampling and desirable resolution of the data once mapped and displayed.

As further shown in FIG. 5, any one or more of miniature pressure sensor cells 225 optionally can be replaced by one or more of alternative sensors cells 278 for sensing data other than mechanical force-type data that is sensed by pressure sensor cells 225. For example, alternative sensor cells include, but are not limited to, the following types of sensor cells: infrared 278A; ultrasonic 278B; x-ray 278C; electromagnetic 278D; nuclear magnetic resonance 278E; and thermal 278F. Data from these alternative sensor cells 278 is handled substantially the same as data from sensor cells 225, including transmitting, sensing, mapping, displaying and analyzing these alternative detectable in the same dynamic, two-dimensional framework of mapping and displaying, measurement and visualization of those mapped sensed data.

These alternative sensor cells 278 can be arranged in arrays in a similar configuration to sensor array 202 and integrated with or without pressure sensor cells 225 on the same substrate as one electronic physical component or chip. Data from these alternative sensor cells 278 is multiplexed, pre-amplified, digitized, organized and transported individually or in any combination (either including or excluding pressure signals from cells 225) to microprocessor 107 and monitor 122 for analysis and display. These alternative sensor cells 278 also can operate under differential pressurization from pressure applicators 202.

Figure 6:
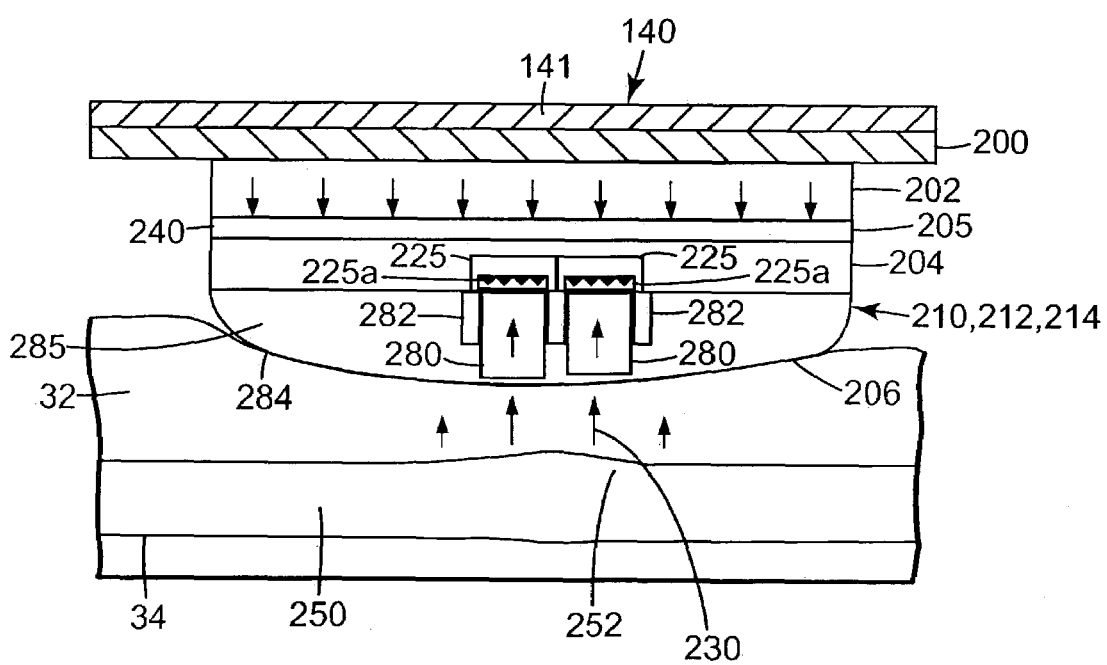
FIG. 6 is a sectional view of a set of pulse probes, according to an embodiment of the present invention.

As shown in FIG. 6, each pulse pressure probe 210, 212, 214 comprises an electrically-driven pressure applicator 202, an on-board signal pre-amplifier/processor 205, an integrated pressure sensor array 204 and a pulse pressure-translating fingertip 206 in an orderly stack oriented towards the skin 30 and tissue 32. Integrated pressure sensor array 204 comprises a plurality of miniaturized pressure sensor cells 225 in a regularly spaced, planner arrangement (as in FIG. 5). Each of the miniaturized pressure sensors 225 senses and measures, via its pressure actuator 225*a*, the local pressure or the total force in summation transmitted by the pulse pressure-translating fingertip 206. In one preferred embodiment of this invention, the pulse pressure-translating fingertip 206 comprises an array of pressure translating rods 280, separated and framed in the planar arrangement via a fixture surrounding 282 and packaged by an outmost flexible skin 284. Pressure translating rods 280 are made of flexible, resilient material such as an elastic rubber material or polymeric material simulating a human fingertip. Each pressure-translating rod 280 is held in direct contact with the skin 30 and tissue 32 and thus, translates the pulse pressure 230 in a total sum of force measurement to the pressure actuator 225a of one miniaturized pressure sensor cell 225.

In an alternate arrangement of the probe shown in FIG. 6, rods 280 are optionally omitted leaving a tip 206 comprising solely a flexible, resilient material such as an elastic rubber material or polymeric material simulating a human finger tips. This material assists in translating the pulse pressure 230 in a continuous distribution to the individual miniaturized pressure sensor cells 225. Finally, another alternate arrangement of the probe shown in FIG. 6 optionally includes completely omitting a pulse pressure translating finger tip 206, wherein the miniaturized pressure sensor cells 225 of pressure sensor array 204 are available for direct contact with the outer skin 30 and tissue 32 to directly sense and measure the pulse pressure 230.

Electrically-driven pressure applicator 222 shown in FIG. 6 is a plate-shaped device that can expand or contract vertically, and thus press the pressure sensor array 204 and translator tip 206 (as well as the on-board signal preprocessor 205) downward against (or pull them up away from) the skin 30 and tissue 32, upon an adaptive input of electrical charge or current for desired pressurization.

Figure 7:
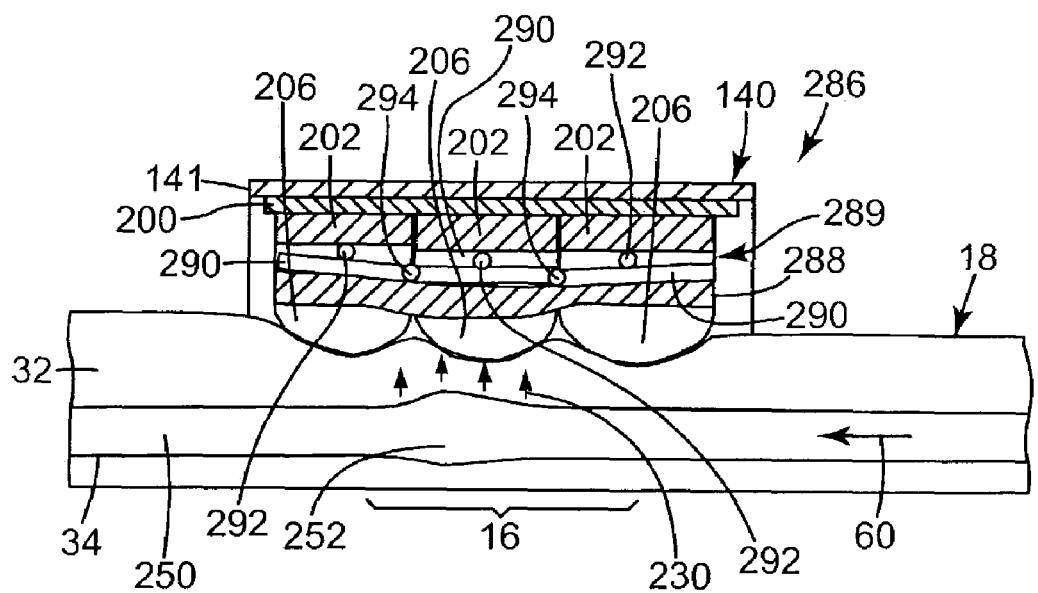
FIG. 7 is a sectional view of a pulse probe of a pulse diagnostic system, according to an embodiment of the present invention.

FIG. 7 illustrates an alternative probe set 286 in which three individual pressure sensor arrays 204 are replaced by a single integrated pressure sensor array 288, which has substantially the same attributes and features as each sensor array 204 except for its size. This single sensor array 288 extends laterally across all three probes 210, 212, 214 as a single flexible substrate that is sandwiched between the set of three translation tips 206 and the set of three electrically-driven pressure applicators 202. In this arrangement, each of three electrical pressure applicators 202 are connected to single sensor pressure array 288 through a force translation system 289 comprising a set of three plates 290 (one for each probe 210, 212, 214) with hinges 294 pivotally connecting plates 290 together. Pivot devices 292 (e.g., balls, cylinder, etc.) are interposed between each plate 290 and each pressure applicator 202 to assist in transmitting force between pressure applicator 202 and single sensor array 288 through force translation plates 290. Pivot devices 292 and hinged plates 290 act together to translate forces between pressure applicators 202 and single sensor array 288 without causing a stress concentration on the single substrate construction of array 288 when a differential pattern of pressure is applied through pressure applicators 202. Accordingly, single flexible sensor array 288 is shared between otherwise distinct, and independently operable, probes 210, 212, 214.

Electrically-driven pressure applicators 202, shown in FIGS. 1-7, can be any type of small electromechanical translation devices (e.g., actuators) which provide mechanical translation of linear planar motion upon adaptive activation instructions. A preferred range of motion extends from 0 to 2 centimeters. The types of translation devices include, but are not limited to miniaturized stepper motors, stacked plate piezoelectric transducers, magnetic inductive transducers, and miniaturized hydraulic pressurization pumps. For example, pressure applicator 202 can be implemented through several alternative arrangements, as will be described in association with FIGS. 8-10.

Electrical pressurization is applied on the pulse pressure mapping probes by an operator using input device 120 (e.g., keyboard) or mouse 124, as previously described. Upon such an instruction from the operator, computing device 106 (including microprocessor 107) generates and transmits a set of pressurization control signals in electrical voltage or current to individual electrical pressure applicators 202 on the pulse map-sensing probes 210, 212, 214 at the desired level of magnitude of pressurization referencing the digital video signal displayed on the monitor. Transmitted through the electronic interconnect cables 108a, 108b, such adaptive control signal inputs in voltage or current activates the electrical pressure applicators 202 to either further press down the remaining portion (i.e., integrated pressure sensor arrays 204 and translating tips 206) of pulse probes 210, 212, 214 against or from arterial vessel 34 (below skin 30), and thereby adjust the level of magnitude of the sensed pulse pressure topography thus sensed and mapped.

Figure 8:
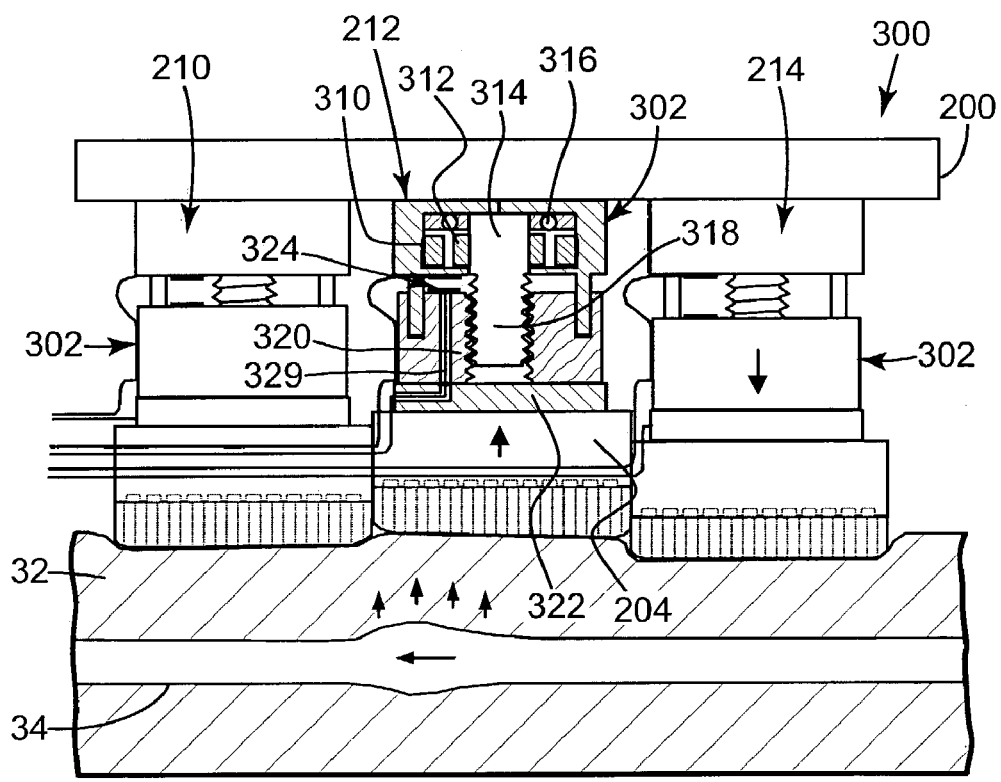
FIG. 8 is a sectional view of a stepper motor translation actuator of a pulse diagnostic system, according to an embodiment of the present invention.

FIG. 8 illustrates a sectional view of pulse probe 300 of the present invention having miniaturized stepper motor 302 acting as its pressure applicator 202. Stepper motor 302 comprises a set of stator poles 310 and mating rotor pole 312, as well as rotating shaft 314 and rotating bearing 316. Stepper motor 302 also includes reciprocating screw-shreds 318, 320 and plate 322. Sensor array 204 is mounted on end of plate 322. Upon electrical actuation of stepper motor 302 by computing device 106, moving plate 322 is translated forward, thereby pushing attached sensor array 204 against the patient's skin 30 at pulse reference point 16. A in-situ capacitance translation probe 329 is nested within female screw-shred 320 and plate 322 for measuring a linear distance that moving plate 322 moves away from rotating shaft 314 and thus, relative to skin 30. This measured linear distance is used for tracking the degree of pressurization exerted onto vessel 34 at pulse reference point 16 by this probe 300.

Figure 9:
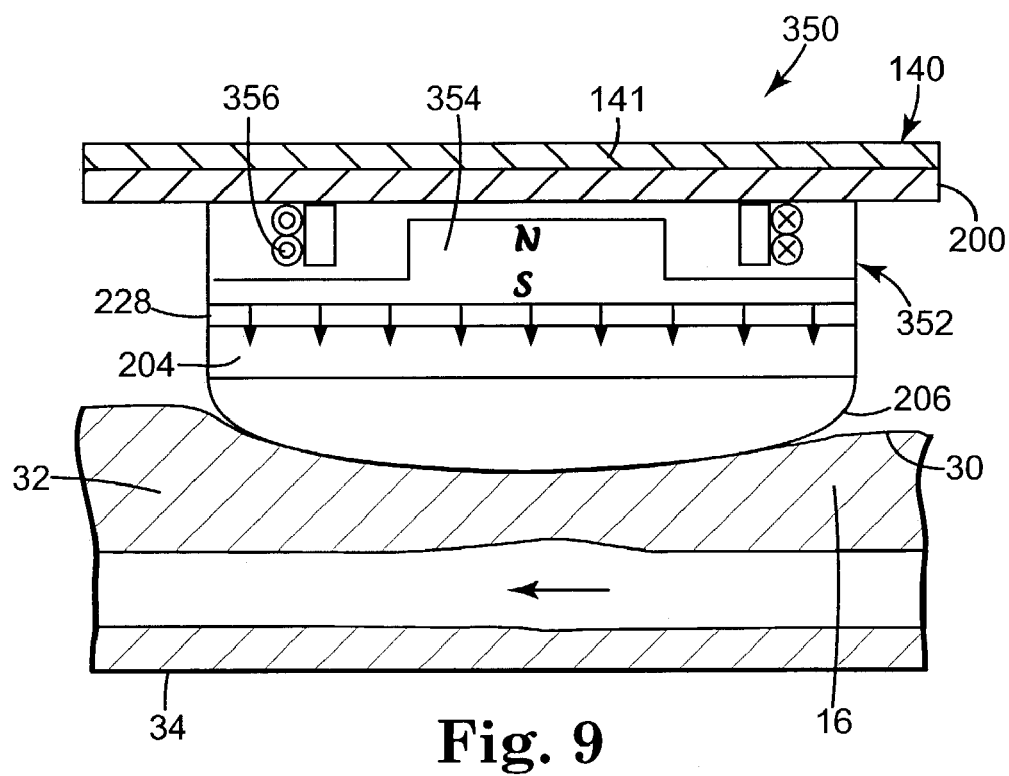
FIG. 9 is a sectional view of an electromagnetic translation actuator of a pulse diagnostic system, according to an embodiment of the present invention.

FIG. 9 illustrates a sectional view of pulse probe 350 of the present invention having magnetic inductive transducer 352 acting as its pressure applicator 202. Magnetic inductive transducer 352 is plate-shaped and sandwiched between backing plate 200 and sensor array 204. Upon application of a current initiated by computing device 106 for actuating pressure applicator 202, magnetic inductive transducer 352 generates vertical movements, to move tip 206 away from or toward vessel 34, through its magnetic fields and interaction between permanent magnet 354 and the magnetic induction from surrounding coil 356.

Figure 10:
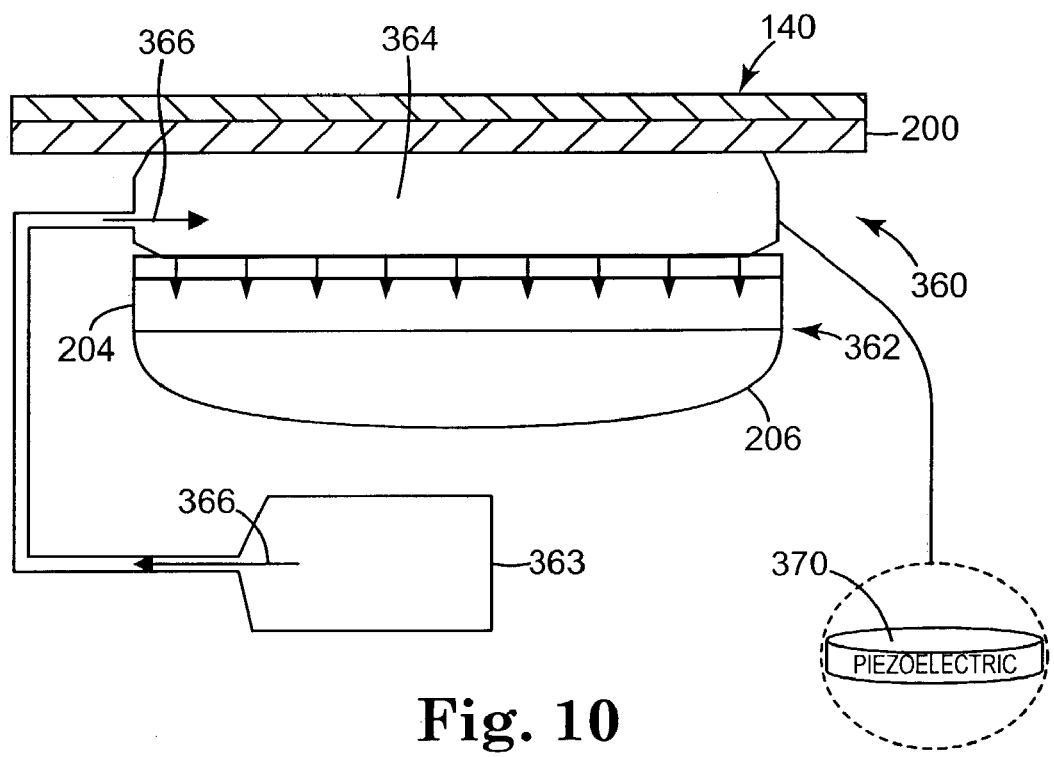
FIG. 10 is sectional view of an inflatable fluid translation actuator of a pulse diagnostic system, according to an embodiment of the present invention.

FIG. 10 illustrates a sectional view of pulse probe 360 of the present invention having hydraulic pressure applicator 362 acting as its pressure applicator 202. Hydraulic pressure applicator 362 incorporates external hydraulic pump 363 as the pressurization driver and pressurization reservoir 364 for holding a hydraulic fluid. Upon application of a current initiated by computing device 106 for actuating pressure applicator 202, external hydraulic pump 363 hydraulically pumps a pressure transmission liquid or gas 366 into or out of the pressurization reservoir 364. An increase in the volume of fluid within reservoir 364 exerts a force to impinge tip 206 further into vessel 34, while a decrease in the volume of fluid effectively reduces the force that tip 34 exerts on vessel 34. This translation of fluid pressure to vessel 34 is enhanced by the relative stability or fixation of stiff fixture panel 200 and flexible cuff 140, which are removably secured to wrist 18 (as shown in FIG. 2), and therefore act as a relatively rigid backing plate to fluid reservoir 364.

Finally, as also shown in FIG. 10, pulse probe 360 of the present invention optionally includes planar piezoelectric transducer 370 for its pressure applicator (e.g., pressure applicator 202) instead of pump system 362, wherein piezoelectric transducer 370 is configured for selective thickness expansion and contraction upon an externally applied electrical charge via computing device 106.

Figure 11:
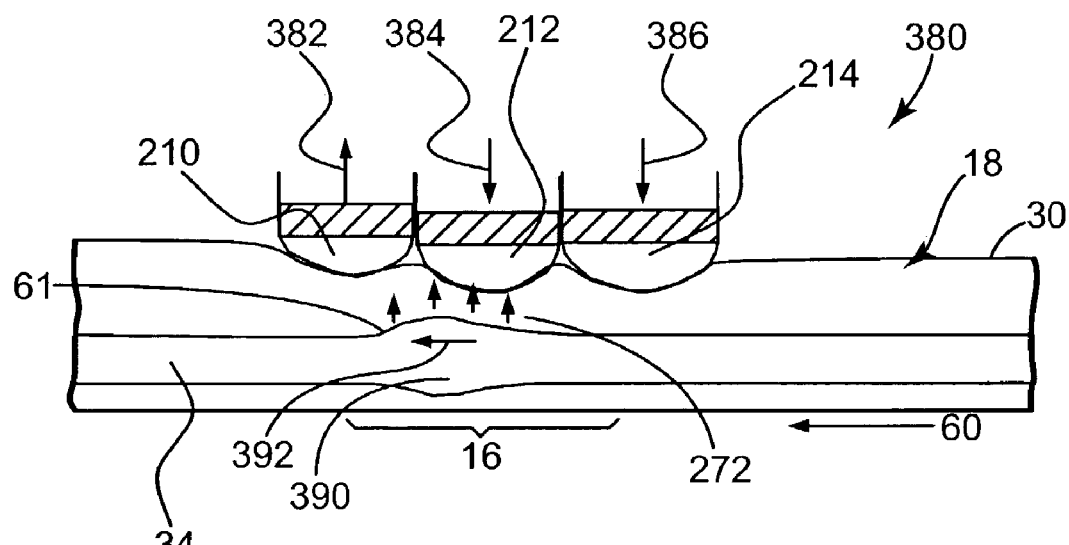
FIG. 11 is a sectional view of an interactive differential pressurization of an arterial vessel using a pulse diagnostic system, according to an embodiment of the present invention.

FIG. 11 schematically depicts each of probes 210, 212, 214, applying a different pressure profile against vessel 34 through skin 30. In particular, first pressure 382, second pressure 384, and third pressure 386 are applied, respectively, through first probe 210, second probe 212, and third probe 214 to apply three different pressures in series along and against vessel 34. First pressure 382, second pressure 384, and third pressure 386 are generated by pressure applicator 202 of each probe 210, 212, 214, when selectively actuated by computing device 106. As seen in FIG. 11, greater pressures that are applied by second and third pressures 384, 386 and a lesser pressure, which is applied by first pressure 382, physically forces the pulse or peak of pulse pressure 45 in arterial vessel 34 downstream, as reflected by shift 61.

While a particular combination of pressures is shown in FIG. 11, any combination of first, second, and third pressures can be applied that vary in direction, as well as amplitude, as dictated by the interest of the practitioner in manipulating pulse pressure. Moreover, as previously described in association with FIGS. 2-3, three-button mouse 124 available to user to allow direct instruction of increase and decrease of pressure, including direction and amplitude.

Figure 12:
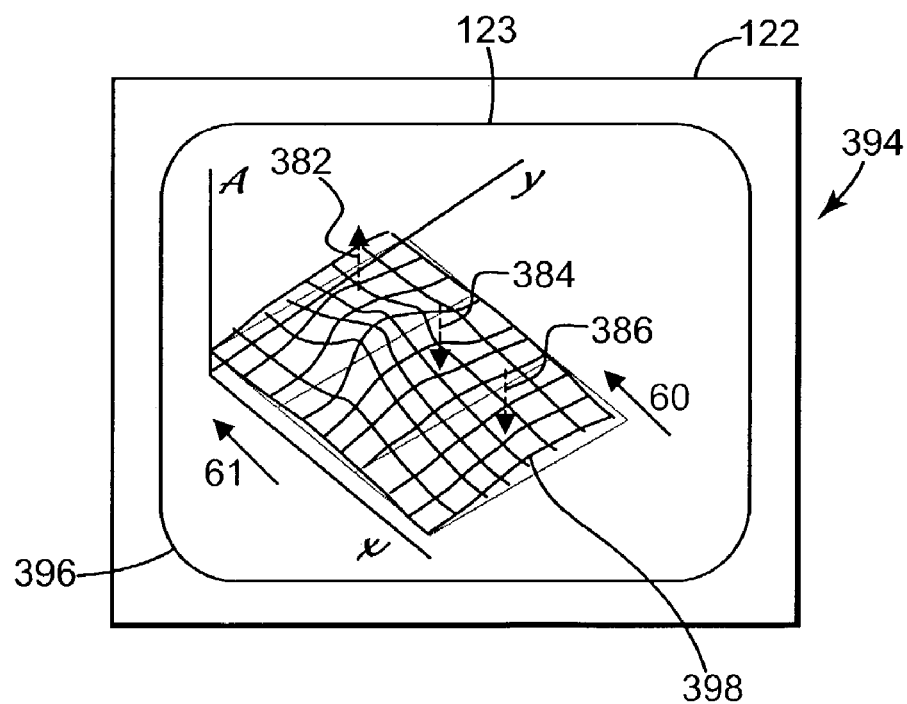
FIG. 12 is a perspective view of pulse pressure topographic map, according to an embodiment of the present invention.

The effect of the differential pressurization applied, as shown in FIG. 11, is illustrated in FIG. 12. FIG. 12 illustrates monitor 122, which displays a pulse pressure topography image and waveform 398 generated by computing device 106 from a digital signal of pulse pressure topography sensed by probes 210, 212, 214. This waveform 398 shows the tendency of a consistent shift of a peak of pulse pressure 392 that corresponds to this differential pressurization. When this differential pressurization is reversed, as when the first pressure 382 is reversed to exert pressure on vessel 34 (and optionally second pressure 384) and third pressure is reversed to lessen pressure on vessel 34, relative to the artery flow 60, the pulse or peak of pulse pressure 390 tends to shift upstream (i.e., proximally) along the artery vessel.

While removable cuff 104 shown in FIG. 2 provides a convenient mechanism for removable securing diagnostic instrument 102 against reference point 16 (e.g., conkuo acupoint), alternative fixation arrangements can be used. For example, a wrist fixture of the present invention can be substituted for removable cuff 104 to facilitate a more stable placement of probes 210, 212, 214 against vessel 34. This wrist fixture is described in association with FIGS. 13, 14 and 15, with each arrangement comprising substantially the same structure in each Figure, except for a focal point from which pressure is generated by the wrist fixture for application against vessel 34 at reference point 16.

Figure 13:
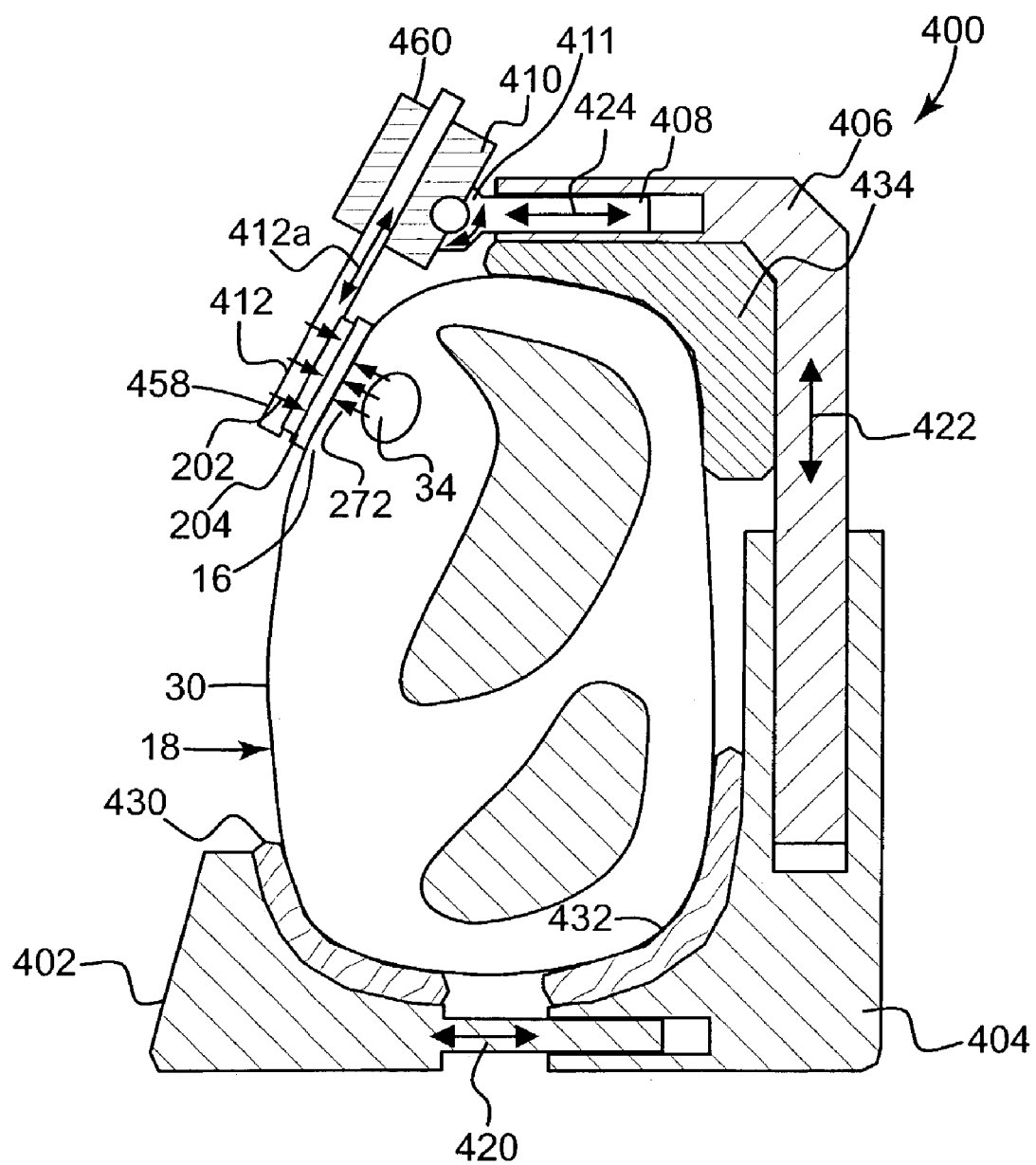
FIG. 13 is a sectional view of a patient's wrist and a wrist fixture of a pulse diagnostic system, according to an embodiment of the present invention.

As shown in FIG. 13, wrist fixture 400 of the present invention provides a generally rigid frame comprising a plurality of relatively movable but releasably lockable plate portions that act together to partially or fully encircle about wrist 18 in a locked configuration. Wrist fixture 400 is configured to place probes 210, 212 and 214 at reference point 16 and arranged to firmly press those sensor probes into skin 30 for engaging artery vessel 34. Wrist fixture 400 includes frame base portions 402 and 404, upper portion 406 with slidable extension 408, header 410, rotator 411, finger 412, and bar 420.

At the bottom of wrist fixture 400, bar 420 extends from base portion 402 to be slidably received by base portion 404, thereby permitting adjustable lateral spacing between connected base portions 402 and 404. Upper portion 406 is slidably engaged within base portion 404, and thereby adjustable in height relative to base portion 204. Header 410 is connected to extension bar 408, for slidable engagement with, and linear movement relative to upper portion 406. A rotator 411 forms a portion of header 410 and/or extension bar 408 and facilitates selective angulation of header 410 relative to upper portion 406 and wrist 18. Finally, finger(s) 412 is slidably extendable from the header 410 for placing sensor array 204 at reference point 16. As further shown in FIG. 13, pressure applicators 202 are mounted at the outer end 458 of finger 412 for directly applying an external force to pulse reference point 16.

Wrist fixture 400 also optionally includes a plurality of cushions 430, 432 and 434 for comfort and to insure that base portions 402, 404 and upper portion 406 fit snugly and firmly about wrist 18. Of course, wrist fixture 400 is optionally sized for other body limbs, such as a lower leg, finger, etc. to apply pressure sensors to other arterial vessels.

Figure 14:
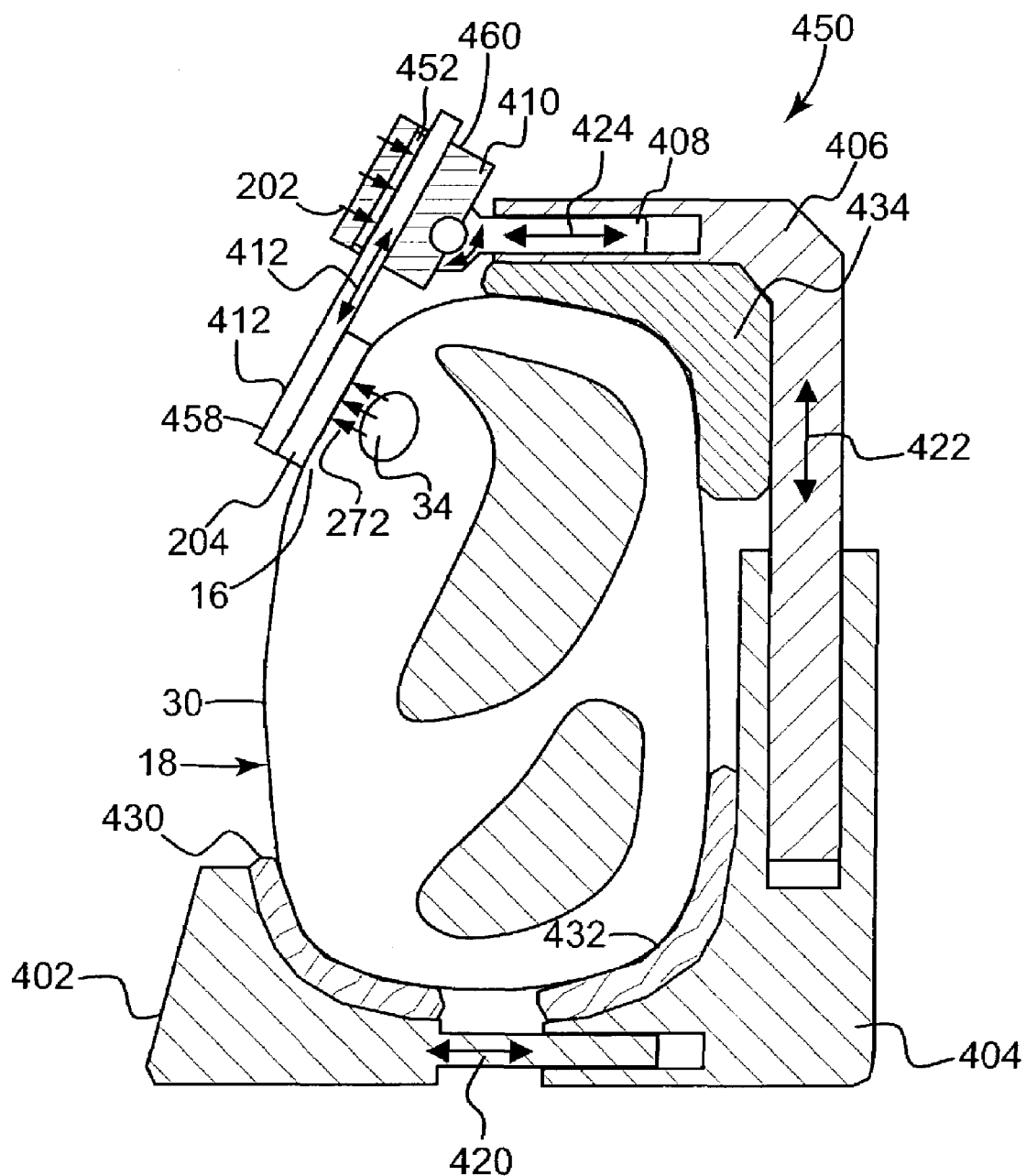
FIG. 14 is a sectional view of a patient's wrist and a wrist fixture of a pulse diagnostic system, according to an embodiment of the present invention.

FIG. 14 illustrates wrist fixture 450, which has substantially the same features and attributes as wrist fixture 400 (FIG. 13). However, wrist fixture 450 provides a focal point for generating pressure by pressure applicators 202 header 410, rather than at outer end 458 of finger 412 as in fixture 400 (FIG. 13). The pressure generated at header 410 is translated down finger 412 to achieve pressurization onto probes 210, 212 and 214 for exertion upon vessel 34 through skin 30.

Figure 15:
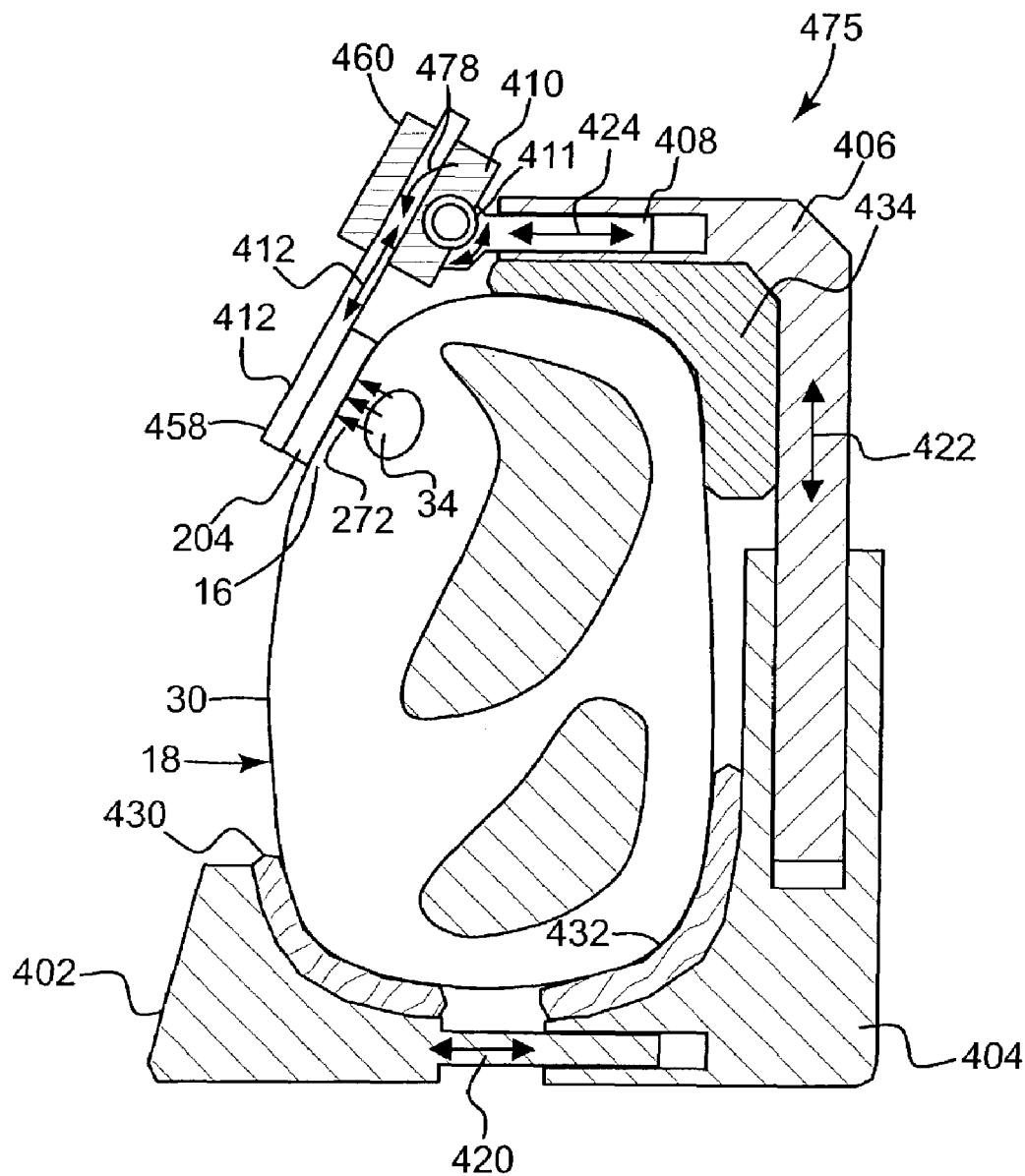
FIG. 15 is a sectional view of a patient's wrist and a wrist fixture of a pulse diagnostic system, according to an embodiment of the present invention.

FIG. 15 illustrates wrist fixture 475, which has substantially the same features and attributes as wrist fixture 400 (FIG. 13). However, wrist fixture 475 provides a focal point for generating pressure by pressure applicator(s) 202 at rotator 411, rather than at outer end 458 of finger 412 as in fixture 400 (FIG. 13). The pressure generated at rotator 411 is applied as a rotational torque about rotator 411 and translated through header 410 and down finger 412 to achieve pressurization onto probes 210, 212 and 214 for exertion upon vessel 34 through skin 30.

Figure 16:
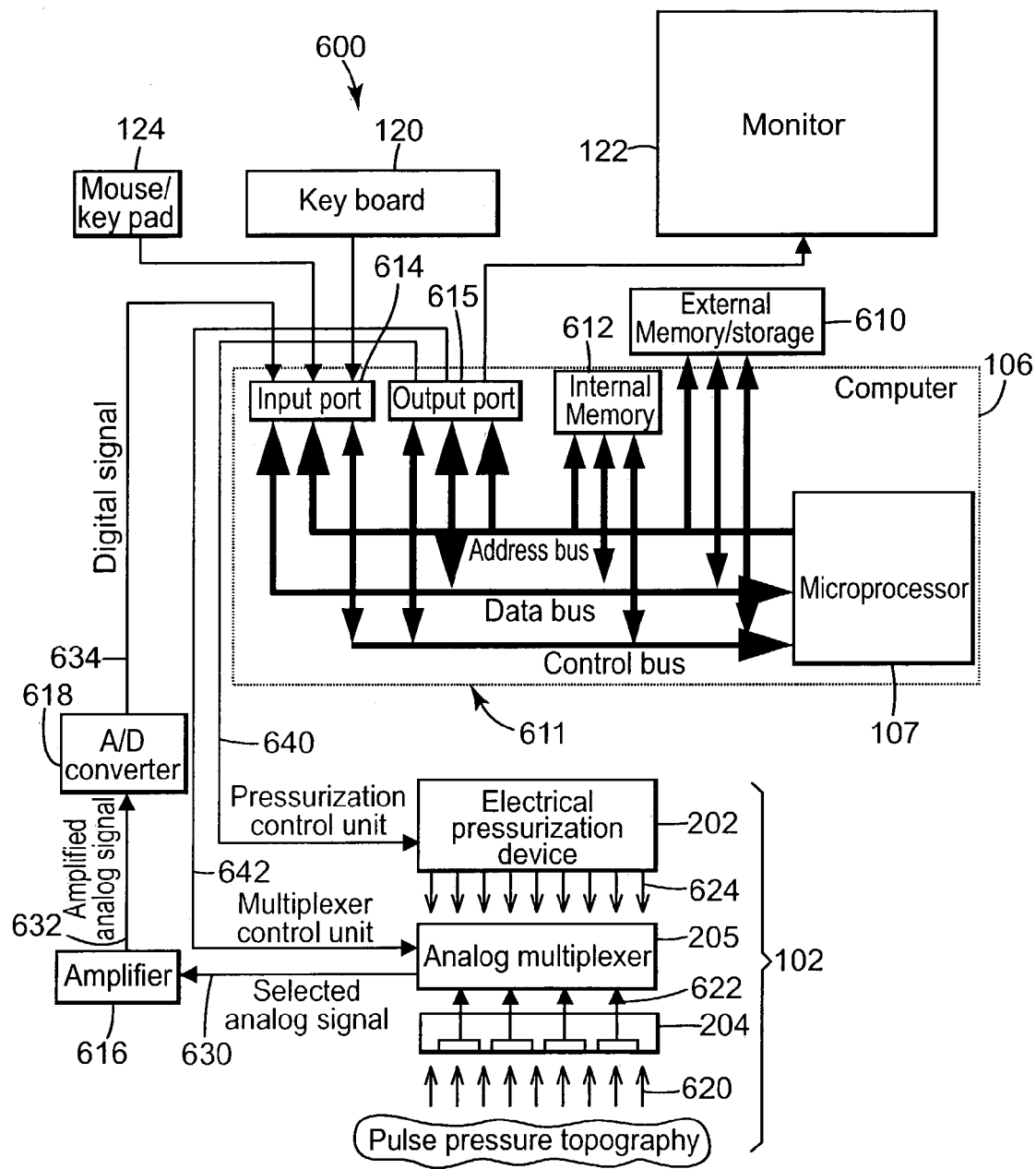
FIG. 16 is a schematic diagram of a pulse diagnostic system, according to an embodiment of the present invention.

System 100 of the present invention as previously shown in FIG. 2 includes diagnostic instrument 102, which acts in cooperation with computing device 106, monitor 122, as well as mouse 124 and input device 120. System 600 of the present invention, as shown in FIG. 16, comprises substantially the same attributes and features as system 100 shown in FIG. 2. However, system 600 shown in FIG. 16 provides a more detailed schematic illustration of the communication, function, and interaction between various components of system 100 of the present invention.

System 600 comprises at least the following components: external memory 610, communication interface 611, internal memory 612, input port 614, output port 615, amplifier 616, analog multiplexer 205, A/D converter 618, as well as previously described computing device 106, microprocessor 107, mouse 124, monitor 122, input device 120, sensor array 204, and pressure applicator 202. System 600 also depicts various signals and pressures including: pulse pressure 620, sensed pulse pressure 622, backside pressurization 624, selected analog signal 630, amplified analog signal 632, digital signal 634, pressurization control signal 640, and multiplexer control signal 642.

The pulse pressure 620 is sensed and converted to the electrical analog signal 630 of pulse pressure by the miniaturized pressure sensor cells 225 on one of the integrated pressure sensor arrays 204. The on-board signal pre-amplifier/processor 205 continuously performs multiplexing (preferably in a raster-scan arrangement of order at much higher frequency than the pulse rate), pre-amplification and analog-to-digital conversion of the analog signal 622 sensed by all the miniaturized pressure sensor cells 225. The on-board signal pre-processor 205 then transmits digital signal 634 of pulse pressure 420 (via the electronic interconnect cable 250, as seen in FIG. 2) to microprocessor 107 in a temporally regulated sequence of order through the input ports 614. The received digital signal of pulse pressure 622 is digitally analyzed and transformed to a digital video signal 123 (FIG. 3), which is then transmitted via communication interface 611 to display monitor 122. The pulse pressure and its two-dimensional topography 230, mapped through the integrated pressure sensor arrays 204, is thus visualized on the monitor 122 as a displayable digital video signal 123 of pulse pressure topography 125 comprising the pulse pressure topography image and waveform and analytical data relating to the dynamic characteristics invisible pulse pressure and its two-dimensional topography 230 obtained through microprocessor 107.

The digital graphic data of pulse pressure topography is a continuous time sequence of multiple image frames over one or more pulse cycles. The set of digital graphic image data of pulse pressure topography is digitally analyzed through microprocessor 107 of computing device 106 to determine the dynamic characteristics of pulse pressure for further use in diagnosing medical conditions of the patient. Those dynamic pulse pressure characteristics include, but are not limited to, the pulse rate or frequency, rhythm, extend of filling, evenness, motility, and amplitude as well as the rate of change in the peak pressure in magnitude. These dynamic pulse pressure characteristics also include the horizontal shifting speeds of the pressure peak under differential pressurization conditions (i.e., pressure applicators 202 applying different levels of pressure through probe tips 206 against arterial vessel 34 through skin 30). Using these dynamic pulse pressure characteristics, the type of pulse can be identified and the strength of pulse can be objectively defined. The numeric and text data on those dynamic characteristics of pulse pressure are then combined with the set of digital image data and transformed to a continuous digital video signal 123 to be displayed on monitor 122.

System 600 preferably includes one or more digital data storage devices as external memory 610 and/or internal memory 612 (besides the volatile memories included in the microprocessor 107), that are physically and electronically connected with the microprocessor 107 via communication interface 130 (shown as interface 611 in FIG. 16). Any digital set of the data collected or generated by the microprocessor 107, such as digital graphic image data of two-dimensional pulse pressure topography and the identification information on the patient, can be permanently (of course and temporally if desired) stored onto one of digital data storage devices 610, 612 for future retrieval, reuse, and transfer.

Internal memory 612 and external memory 610 comprise digital data storage devices including, but not limited to, magnetic tape, floppy disk, optical disk or hard disk drives and flash memory cards capable of permanently storing as many sets of digital data critical to the patient's pulse condition and diagnosis as desired. This digital data includes, but is not limited to, the digital signal of pulse pressure, the digital graphic data of pulse pressure topography, numeric and text data on the dynamic characteristics, as well as the digital video signal of pulse pressure topographic evolution.

Figure 17:
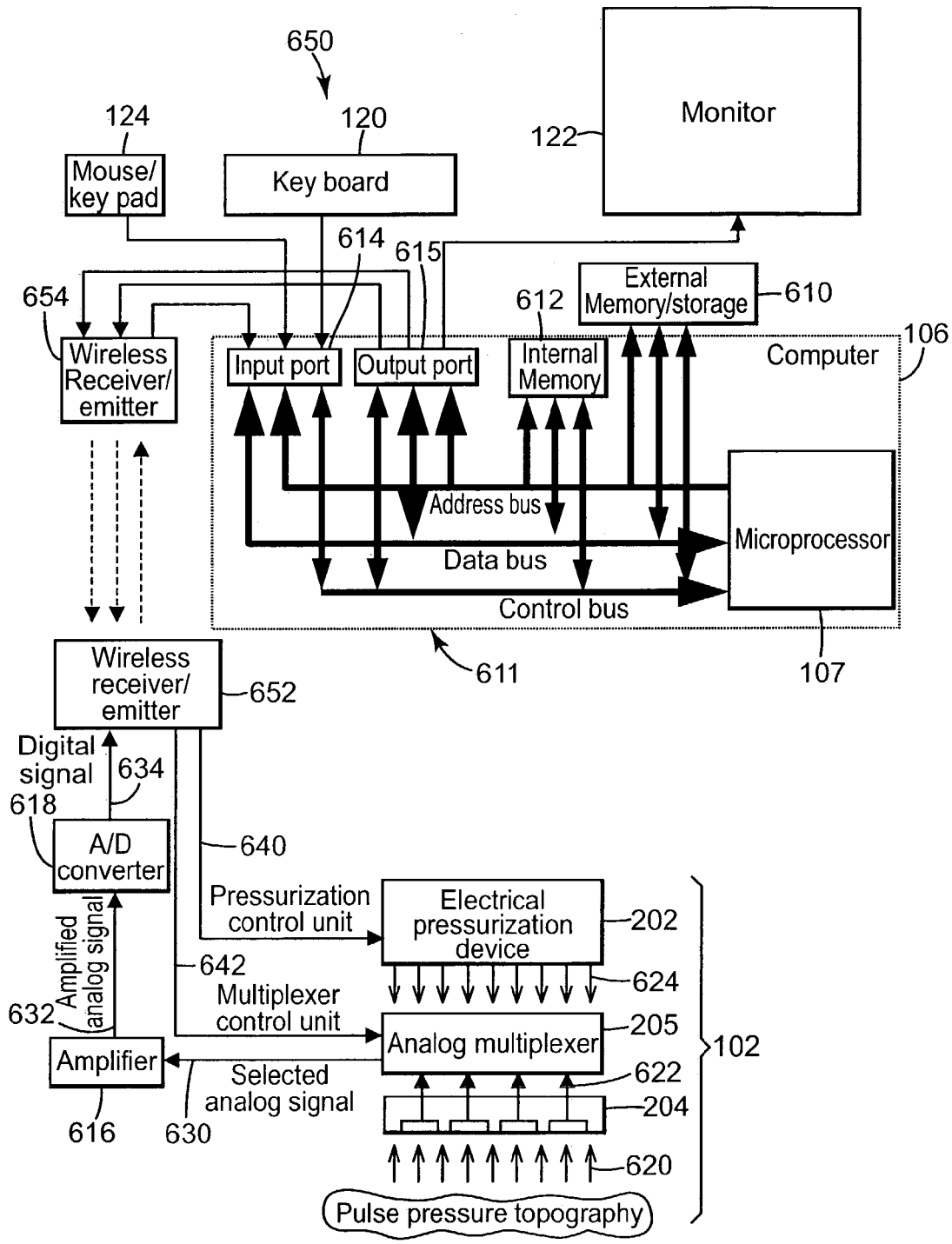
FIG. 17 is a schematic diagram of a pulse diagnostic system, according to an embodiment of the present invention.

As shown in FIG. 17, system 600 optionally can be modified into system 650, having substantially the same attributes and features as system 600 except using wireless transceivers 652, 654 to perform two-way transfer of digital signal data between computing device 106 and diagnostic instrument 102. In particular, in system 650 as a signal, such as digital signal 634, is wirelessly transmitted and received, respectively, between wireless transceiver 652 (e.g., wireless emitter and receiver combination) and wireless transceiver 654. This wireless transmission path is used both for transmitting collected data from diagnostic instrument 102 to computing device 106, and for transmitting control instructions from computing device 106 to diagnostic instrument 102.

Using data collected from diagnostic instrument 102 and computing device 106, a method of the present invention includes producing a digital video image of two-dimensional matrix of the calculated pressure values from a matrix of locations corresponding to locations of individual pressure sensor cells 225 of array (FIG. 5). This data matrix comprises, over the duration of one or more captured pulse cycles (points in time), discrete values of the pulse pressure topography 230 at those discrete locations of arterial pulse reference region 16 a plurality of rows in transverse direction (e.g., represented by x axis) and a plurality of columns in longitudinal direction (e.g., represented by y axis). From this matrix, microprocessor 107 can identify a maximum or peak pressure of the pulse pressure topography 230 for a given point in time. During the short silent period of one pulse cycle, the pulse pressure topography 230 is a relatively flat terrain with no abrupt hump of high pressure points. Moreover, at one selected moment of measurement over the silent period when the pulse pressure is mapped within the silent period, a referencing pressure value can be calculated.

With the reference pressure establishing a baseline, a rate of increase in the peak pressure of the pulse pressure topography 230 is evaluated quantitatively to further derive numerical information on the strength of pulse pressure. Thus, using an established baseline of pulse pressure data, a user can quantitatively and objectively compare the "strengths" of human pulses at pulse reference point, while accounting for dynamic application pressurization at pulse reference point during such measurement. By selectively changing application of pressure, modify pulse pressure topography.

Certain dynamic characteristics of the pressure peak, including its moving location, can also be readily derived numerically as objective parameters for diagnostic purposes. For example, the horizontal speeds of the pressure peak's movement in the arterial pulse reference point 16 can be determined using well-known mathematical algorithms. Using this matrix of pulse pressure topography, user can ascertain various conditions about physiologic condition of subject.

For example, the number of the pulse map-sensing probes, or "electronic fingers", is not limited to two or three in a row, arranged parallel to the arterial vessel. Moreover, the system is not just limited for sensing and mapping, and analyzing and displaying the pressure pulse at a human wrist. With appropriate modification of the flexible bandage of the pulse map-sensing and interactive pressurization assembly, it can be applied to other pulse points on a human body such as two on the human's upper neck and even to certain pulse points of animals.

A system and method of the present invention detects, maps, transmits, displays, analyzes and/or characterizes a two-dimensional pulse pressure topography, and its dynamic evolution over time, of a human pulse within an arterial vessel. Moreover, this system and method allows interactive, controllable and precise pressurization against the arterial vessel independently in each individual region of vessel pulse detection. This system and method is expected to bring an objective assessment to pulse diagnostics using the three-finger method of pulse pressure detection and evaluation.

While specific embodiments have been illustrated and described, herein for purposes of description of the preferred embodiment, it will be appreciated by those of ordinary skill in the art that a wide variety of alternate and/or equivalent implementations may be substituted for the specific embodiments shown and described without departing from the scope of the present invention. Those with skill in the chemical, mechanical, electromechanical, electrical, medical, and computer arts will readily appreciate that the present invention may be implemented in a very wide variety of embodiments. This application is intended to cover any adaptations or variations of the preferred embodiments discussed herein. Therefore, it is manifestly intended that this invention be limited only by the claims and the equivalents thereof.

What is claimed is:

1. A method of sensing a subject's blood pressure pulse comprising:
    non-invasively sensing, with an array of pressure sensors in contact against a skin surface over an arterial vessel, an arterial blood pressure pulse of the subject's blood pressure in the arterial vessel through multiple pulse cycles of the subject's arterial blood pressure pulse; and
    selectively pressing against the arterial vessel, during the sensing of the arterial blood pressure pulse through the multiple pulse cycles of the subject's arterial blood pressure pulse, at the location of each of the sensors of the array via at least two probes aligned in series along the arterial vessel with each respective probe dynamically exerting a different external force against the arterial vessel to cause a local artificial increase in the sensed arterial blood pressure pulse, wherein selectively pressing against the arterial vessel comprises:
        manipulating a finger-controllable input device to dynamically select the external force applied to the arterial vessel through the probes and processing the manipulations through a computing device to electrically drive a pressure actuator of the probes to cause the selected external force to be applied against the arterial vessel; and
        arranging the finger-controllable input device as an array of buttons with each button directly corresponding to one of the respective probes so that actuation of one of the respective button selects, and causes, the external force to be applied through one of the respective probes directly corresponding to the actuated button.

2. A method of sensing a subject's blood pressure pulse comprising:
    non-invasively sensing, with an array of pressure sensors in contact against a skin surface over an arterial vessel, an arterial blood pressure pulse of the subject's blood pressure in the arterial vessel through multiple pulse cycles of the subject's arterial blood pressure pulse, wherein non-invasively sensing the arterial blood pressure pulse comprises:
        quantitatively measuring, over time, a plurality of first pulse pressures of the arterial vessel laterally spaced apart from each other along a first direction generally transverse to a longitudinal axis of the arterial vessel and a plurality of second pulse pressures of the arterial vessel longitudinally spaced apart from each other along a second direction generally parallel to a longitudinal axis of the arterial vessel; and
        storing the quantitatively measured respective first pulse pressures and respective second pulse pressures as data and displaying the data as a three-dimensional graphic representation mapping the pulse pressure topography of the arterial vessel with the three-dimensional graphic representation including a time parameter, an amplitude profile of the first pulse pressures and an amplitude profile of the second pulse pressures; and
    selectively pressing against the arterial vessel, during the sensing of the arterial blood pressure pulse through the multiple pulse cycles of the subject's arterial blood pressure pulse, at the location of each of the sensors of the array via at least two probes aligned in series along the arterial vessel with each respective probe dynamically exerting a different external force against the arterial vessel to cause a local artificial increase in the sensed arterial blood pressure pulse.

3. The method of claim 2 wherein the selective pressing against the arterial vessel comprises:
    selectively driving a pulse peak shift of the arterial blood pressure pulse linearly along the arterial vessel around a pulse reference point by dynamically pressing each probe against the arterial vessel; and
    wherein sensing the pulse pressure comprises:
    quantitatively sensing and measuring a dynamic temporal evolution of the arterial blood pressure pulse around the pulse reference point and graphically displaying a three-dimensional topography of the dynamic temporal evolution of the arterial blood pressure pulse.

4. The method of claim 2 wherein sensing the arterial blood pressure pulse comprises:
    measuring the arterial blood pressure pulse, prior to selective pressing against the arterial vessel with the probes or between instances of selective pressing against the arterial vessel, to establish a baseline pulse pressure pattern.

5. The method of claim 2 wherein sensing the arterial blood pressure pulse comprises:
    removably securing the array of pressure sensors relative to the arterial vessel via at least one of:
        a removable wraparound cuff that carries the sensor array configured and sized for removably wrapping around a body limb carrying the arterial vessel; and
        a relatively rigid fixation frame into which a body limb is removably insertable.

6. The method of claim 2 wherein selectively pressing against the arterial vessel comprises:
    providing the probes with an electrically driven pressure applicator for applying the pressure to the arterial vessel, the pressure applicator including at least one of:
    a stepper motor;
    an electromagnetic transducer;
    an inflatable fluid pump; and
    a piezoelectric transducer.

7. A pulse diagnostic system comprising:
an instrument including a plurality of probes connected together and aligned laterally in series, with each probe configured for contacting a skin surface of a body limb over an arterial vessel, each probe including:
  a pressure sensor configured for sensing an arterial blood pressure pulse of the arterial vessel; and
  an electrically-driven pressure applicator mounted in vertical alignment relative to the pressure sensor and configured for applying an external force vertically through the pressure sensors to apply pressure vertically on top of and against the arterial vessel through the skin surface;
a controller in electrical communication with the instrument and configured for selectively controlling the external force applied by each probe and configured for receiving pulse pressure data sensed by the pressure sensors of the respective probes, wherein the controller comprises a digital microprocessor and at least one of an internal memory and an external memory;
a display monitor; and
an input device comprising a hand controllable pointing device including an array of push-buttons with each respective push-button directly corresponding to one of the respective probes, to permit selective application of the external force by the pressure applicator of each probe by pressing the respective push button of the hand controllable pointing device.

8. A method of sensing a pulse comprising:
non-invasively sensing, with an array of plurality of pressure sensors in contact against a skin surface over an arterial vessel, a pulse pressure of the arterial vessel;
selectively pressing against the arterial vessel, during the sensing of the pulse pressure, at the location of each of the sensors of the array with at least two probes aligned in series along the arterial vessel with each probe dynamically exerting a different pressure against the arterial vessel to cause a local artificial increase in the pulse pressure, including selectively driving a pulse peak shift of the pulse pressure linearly along the arterial vessel around a pulse reference point by dynamically pressing each probe against the arterial vessel, including selecting the pulse reference point as a Cunkou acupoint along the arterial vessel of a wrist; and
quantitatively sensing and measuring a dynamic temporal evolution of the pulse pressure topography around the pulse reference point.

9. A pulse diagnostic instrument including:
a plurality of probes connected together and aligned laterally in series, with each probe configured for contacting a skin surface of a body limb adjacent an arterial vessel and each probe including:
  a single pressure sensor array configured for sensing a pulse pressure of the arterial vessel and configured on a single substrate that extends as a layer, as a portion of and through all the probes;
  an electrically-driven pressure applicator mounted to the single pressure sensor array and configured for applying an external force through the single pressure sensor array to apply pressure against the arterial vessel through the skin surface; and
  a force translation mechanism interposed between the single pressure sensor array and the pressure applicator of each respective probe, and configured for translating a different force from the pressure applicator of each respective probe to a corresponding portion of the single pressure sensor array in a substantially uniform pressure distribution, wherein the force translation mechanism comprises:
    a plurality of plates, with each plate interposed between a pressure applicator of each probe and a portion of the single pressure sensor array of each probe, and the plates being pivotally hinged together in a lateral arrangement; and
    a plurality of pivot members, with at least one pivot member being disposed between the plate and the pressure applicator of each probe.

* * * * *